United States Patent
Li et al.

(10) Patent No.: US 7,902,380 B2
(45) Date of Patent: Mar. 8, 2011

(54) PROCESS FOR THE PREPARATION OF (S)-ALPHA-ETHYL-2-OXO-1-PYRROLIDINE-ACETAMIDE AND (R)-ALPHA-ETHYL-2-OXO-PYRROLIDINE-ACETAMIDE

(75) Inventors: Yuan Qiang Li, Shanghai (CN);
Zhi-Xian Wang, Brantford (CA);
Bhaskar Reddy Guntoori, Brantford (CA)

(73) Assignee: Apotex Pharmachem Inc., Brantford (CA)

( * ) Notice: Subject to any disclaimer, the term of this patent is extended or adjusted under 35 U.S.C. 154(b) by 532 days.

(21) Appl. No.: 11/667,824

(22) PCT Filed: Nov. 21, 2005

(86) PCT No.: PCT/CA2005/001758
§ 371 (c)(1),
(2), (4) Date: Mar. 24, 2008

(87) PCT Pub. No.: WO2006/053441
PCT Pub. Date: May 26, 2006

(65) Prior Publication Data
US 2009/0069575 A1 Mar. 12, 2009

(30) Foreign Application Priority Data
Nov. 22, 2004 (CA) .................................. 2,488,325

(51) Int. Cl.
*C07D 207/12* (2006.01)
(52) U.S. Cl. ......................................................... 548/551
(58) Field of Classification Search .................... 548/551
See application file for complete search history.

(56) References Cited

U.S. PATENT DOCUMENTS

| | | | |
|---|---|---|---|
| 4,696,942 A | 9/1987 | Gobert et al. | |
| 4,696,943 A | 9/1987 | Gobert et al. | |
| 4,837,224 A * | 6/1989 | Gobert et al. | 514/424 |
| 6,107,492 A | 8/2000 | Futagawa et al. | |
| 6,124,473 A | 9/2000 | Cavoy et al. | |
| 2002/0042508 A1 | 4/2002 | Boaz et al. | |
| 2003/0040631 A1 | 2/2003 | Surtees et al. | |

FOREIGN PATENT DOCUMENTS

| | | |
|---|---|---|
| GB | 1309692 | 4/1973 |
| GB | 2225322 | 5/1990 |
| WO | WO 03/014080 A2 | 2/2003 |
| WO | WO 03/014080 A3 | 2/2003 |
| WO | WO 2004/069796 A2 | 8/2004 |
| WO | WO 2004/069796 A3 | 8/2004 |

OTHER PUBLICATIONS

Conclusions and future prospects [online]. retrieved from the internet on May 9, 2010. URL: http://dissertations.ub.rug.nl/FILES/faculties/science/2002/j.w.nieuwenhuijzen/c7.pdf.*
Wilen, Samuel H.; Strategies in Optical Resolutions.; Tetrahedron (1997), vol. 33: pp. 2725-2736.
Henkler, G. et al.; Fortschritte auf dem Gebiet der Arzneimittelentwicklung.; Die Pharmazie (1982), 37/11: pp. 753-765.
Valenta, V. et al.; Potential Nootropic Agents: Synthesis of a Series of . . . Piperazides.; Collect. Czech. Chem. Commun. (vol. 55) 1990: pp. 1614-1629.
Ebbers et al., Tetrahedron, 53(28), 9417-9476, (1997).
Prous, et al., Drugs of the Future, 19(2), p. 111-113, (1994).

* cited by examiner

*Primary Examiner* — Shawquia Young

(57) ABSTRACT

A process provided for the preparation of the (S)- and (R)-alpha- ethyl-2-oxo-1-pyrrolidineacetamide of formula:(1) from (RS)-alpha-ethyl-2-oxo-1-pyrrolidineacetic acid of formula:(2) comprising: i) combining the (RS)-2 with a chiral base (resolving agent) in a resolution solvent and crystallizing from the said mixture the diastereomeric salt of (S)- or (R)-2 and chiral base; ii) regenerating (S)- or (R)-2 from the crystallized diastereomeric salt by treating with a suitable acid or acidic ion-exchange resin; iii) optionally regenerating (R)- or (S)-2 or their mixture (predominantly one enantiomer) from the crystallization mother liquor by treating with a suitable acid or acidic ion-exchange resin; iv) optionally epimerizing (RS)-2 by treating (R)- or (S)-2 or their mixture (predominantly one enantiomer) of step iii with an acid anhydride; V) optionally converting (RS)-2 of step iv into enantiomerically enriched (S)- or (R)-2 through steps i and ii; vi) formation of the mixed anhydride by reacting (R)- or (S)-2 with an alkyl or aryl sulfonyl halogen compound RSO2X in the presence of a suitable base; and vii) reacting the mixed anhydride with ammonia; wherein R represents C 1 to C 15 alkyl or aryl groups such as methyl, ethyl, p-toluenyl, 2,4,6-trimethylbenzyl, 2,4,6-trichloribenzyl, and X represents a halogen atom such as F, Cl and Br atoms.

(I)

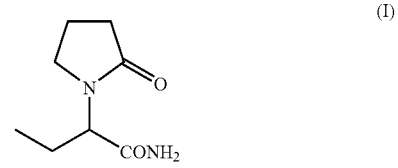

(II)

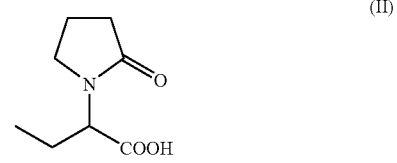

14 Claims, No Drawings

PROCESS FOR THE PREPARATION OF (S)-ALPHA-ETHYL-2-OXO-1-PYRROLIDINE-ACETAMIDE AND (R)-ALPHA-ETHYL-2-OXO-PYRROLIDINE-ACETAMIDE

FIELD OF THE INVENTION

An improved and novel process for the preparation of enantiomerically enriched (S)-alpha-ethyl-2-oxo-1-pyrrolidineacetamide and (R)-alpha-ethyl-2-oxo-1-pyrrolidineacetamide.

BACKGROUND OF THE INVENTION

Alpha-ethyl-2-oxo-1-pyrrolidineacetamide(etiracetam) (1), disclosed in British Pat. No. 1309692, can be used for treatment of motion sickness, hyperkinesias, hypertonia and epilepsy. It is also known that 1 possesses a protective activity against aggressions of the central nerve system caused by hypoxias, cerebral ischemia etc. (Pharmazie, 37/11, (1982), 753-756).

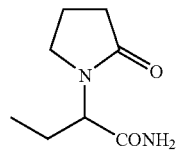

1

Further research reported in U.S. Pat. No. 4,696,943 reveals that the isolated laevorotatory enantiomer (S)-alpha-ethyl-2-oxo-1-pyrrolidineacetamide ((S)-1), which is known as levetiracetam, is more active than its racemic mixture by 1) having 10 fold higher protective activity against hypoxia, and 2) having 4 fold higher protective activity against ischemia.

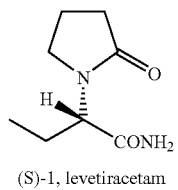

(S)-1, levetiracetam

As a result of these properties, levetiracetam has been indicated as more suitable than the racemic form for the treatment and prevention of hypoia and ischemic type aggressions of the central nervous system.

On the other hand, U.S. Pat. No. 4,696,942 disclosed that the corresponding (R)-enantiomer, (R)-alpha-ethyl-2-oxo-1-pyrrolidineacetamide ((R)-1), is better suited for the treatment of memory disorder. This distinguishes it from the racemic form or its S enantiomer.

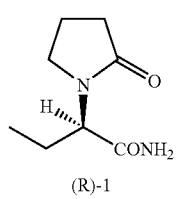

(R)-1

The differentiated medicinal properties of the S and R single enantiomer of 1 enable them to be individually useful for the treatment of different kinds of diseases. Thus, highly enantioselective syntheses of optically pure S and R alpha-ethyl-2-oxo-1-pyrrolidineacetamides are necessary.

Several prior art techniques for the preparation of single (S)— and (R) enantiomers of 1 have been reported.

An optical separation of (S)— and (R)-1 from the racemate by using preparative chiral high performance liquid chromatography or continuous simulated moving bed (SMB) chromatography is disclosed in U.S. Pat. No. 6,124,473. However, preparative HPLC is not desirable for large scale preparation, and SMB is an emerging technology that is not yet widely available in the chemical industry. Also, the initial cost of an SMB system is very high.

Patent GB 2,225,322 describes a process for the preparation of (S)-1 starting with L-methionine, by hydrogenolysis of the intermediate (S)-alpha-[2-(methylthio)ethyl]2-oxo-1-pyrrolidineacetamide by the desulphurizing agent Raney nickel in large excess. Raney nickel is a hazardous material, and may cause serious safety problems during large scale production. Also, while this process is suitable for the (S)-1 compound since L-methionine is inexpensive, the (R)-1 compound using this process is not economical since D-methionine is very expensive.

The enantioselective synthesis of both the (S)— and (R) enantiomers of 1 were disclosed in the U.S. Pat. No. 4,696,942 and U.S. Pat. No. 4,696,943 by the following processes respectively: a) optical resolution of alpha-ethyl-2-oxo-1-pyrrolidineacetic acid, activation of the chiral alpha-ethyl-2-oxo-1-pyrrolidineacetic acid with an alkylhaloformate and subsequent reaction with ammonia; b) cyclizing the chiral S or R amino-butanamide. In the former process, although optical resolution of racemic alpha-ethyl-2-oxo-1-pyrrolidineacetic acid gave (S) or (R)-alpha-ethyl-2-oxo-1-pyrrolidineacetic acid with satisfactory optical purity, this resolution provides less than 50% yield of the desired enantiomer, with the remaining (more than 50%) isomer mixture being discarded as a waste. Also, the amide formation step has to be performed at a very low temperature, normally between −30 to −40° C. to prevent epimerization, which is not convenient for large scale preparation. The latter process presents a drawback with the fact that the required enantiomeric precursors, (S)— and (R)-4-[[1-aminocarbonyl)propyl]amino]butyrate or (S)— and (R)—N-[1-(aminocarbonyl)propyl]4-halobutanamide, for the cyclization are not readily available.

Thus, when scaling up, there is a need for a more robust and cost-effective process for the preparation of both (S) and (R)-1, which overcomes the deficiencies of the prior art.

SUMMARY OF THE INVENTION

The present invention provides a novel commercial process for the preparation of both the (S)— and (R)-enantiomers of alpha-ethyl-2-oxo-1-pyrrolidineacetamide of formula 1 from (RS)-alpha-ethyl-2-oxo-1-pyrrolidineacetic acid of formula 2.

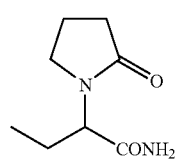

1

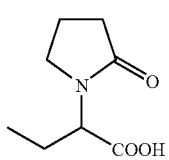

The following is an exemplary scheme of the process:

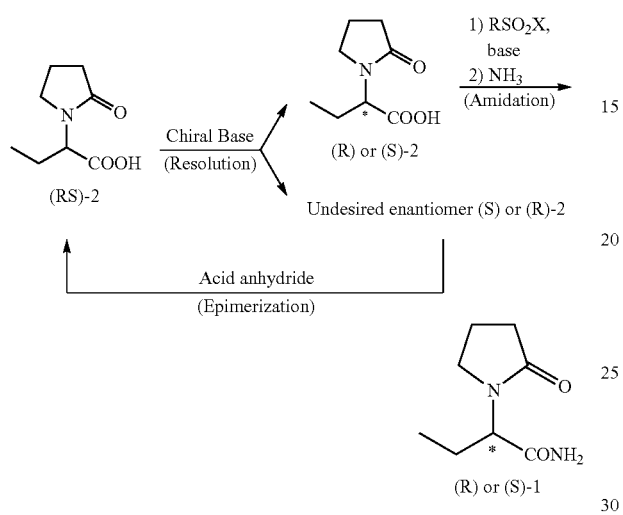

The optical resolution of 2 may be carried out by, for example, the formation of a salt of (S)-2 with the optically active base (R)-alpha-methylbenzylamine or dehydroabietylamine (S. H. Wilen et al. Tetrahedron, 33, (1997), 2725-2736). Likewise, the (R)-2 can be prepared by forming the salt with (S)-alpha-methylbenzylamine. The racemic (RS)-2 used as starting material can be prepared by the known procedure described in GB 1309692.

Surprisingly we have found that the undesired (R) or (S)-alpha-ethyl-2-oxo-1-pyrrolidineacetic acid or their mixture can be epimerized by treating it with an acid anhydride, preferably acetic anhydride, propionic anhydride and butyric anhydride, to furnish a mixture of (R) and (S)-alpha-ethyl-2-oxo-1-pyrrolidineacetic acid in excellent yield. The recovered (RS)-alpha-ethyl-2-oxo-1-pyrrolidineacetic acid can be optically resolved by the same procedure above. In this way, we are able to obtain almost complete conversion of the (RS)-alpha-ethyl-2-oxo-1-pyrrolidineacetic acid to the desired (R) or (S)-alpha-ethyl-2-oxo-1-pyrrolidineacetic acid.

We have also found a novel and efficient process for the production of (S)— and (R)-enantiomers of alpha-ethyl-2-oxo-1-pyrrolidineacetamide from (S) or (R)-alpha-ethyl-2-oxo-1-pyrrolidineacetic acid by converting the acid to a mixed anhydride (a new intermediate compound) using for example, an alkyl or aryl sulfonyl halogen compound followed by treatment with ammonia.

The new process has the following advantages:
1) The reagents used in the process are inexpensive and readily available.
2) Reactions are carried out under mild conditions.
3) The potential recovery yield of (S) or (R)-2 can be more than 50%.
4) Amidation proceeds in high yield with little to no loss of enantiomeric purity.
5) The process is amenable for large-scale production.

DETAILED DESCRIPTION OF ASPECTS OF THE INVENTION

According to one aspect of the invention, a process is provided for the preparation of enantiomerically enriched (R)— or (S)-alpha-ethyl-2-oxo-1-pyrrolidineacetic acid of formula 2 via the resolution of (RS)-2 and recycling of the undesired enantiomer or enantiomeric mixture (predominantly one enantiomer) of 2 by epimerization with an acid anhydride. The process comprises:

i) combining the (RS)-2 with a chiral base (resolving agent) in a resolution solvent and crystallizing from the said mixture the diastereomeric salt of (S)— or (R)-2 and chiral base;

ii) regenerating (S)— or (R)-2 from the crystallized diastereomeric salt by treating with a suitable acid or acidic ion-exchange resin;

iii) regenerating (R)— or (S)-2 or their mixture (predominantly one enantiomer) from the crystallization mother liquor by treating with a suitable acid or acidic ion-exchange resin;

iv) epimerizing (RS)-2 via treating (R)— or (S)-2 or their mixture (predominantly one enantiomer) of step iii with an acid anhydride;

v) optionally converting (RS)-2 of step iv into enantiomerically enriched (S)— or (R)-2 through steps i and ii.

This process is depicted below:

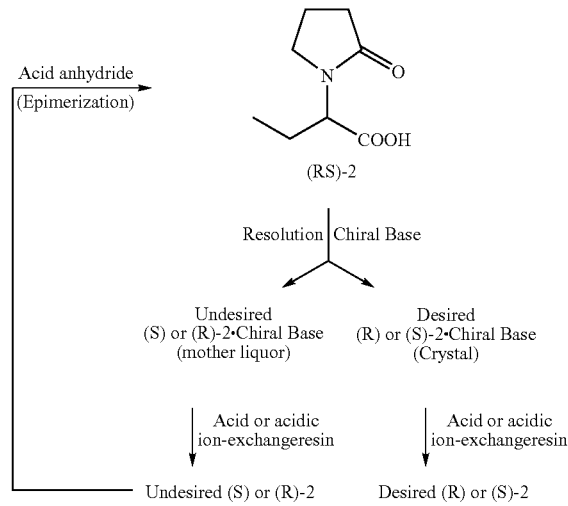

Suitable resolving agents include optically pure bases such as alpha-methylbenzylamine and dehydroabietylamine, of which alpha-methylbenzylamine is preferred. (S)-2 can be prepared by forming the salt with (R)-alpha-methylbenzylamine and the (R)-2 can be prepared by forming the salt with (S)-alpha-methylbenzylamine.

Suitable resolution solvents include water, C1 to C7 alcohols such as methanol, ethanol, isopropanol and butanols, C3 to C7 ketones such as acetone and methyl isobutyl ketone, C2 to C7 nitriles such as acetonitrile, aromatic solvents such as toluene and xylenes, and their mixtures, of which toluene, isopropanol, water and their mixtures are preferred.

The resolution can be carried out in the presence or absence of an organic base. Suitable bases include trialkylamine such as trimethylamine, triethylamine and N,N-diisopropylethylamine, pyridine and the like, of which triethylamine and N,N-diisopropylethylamine are preferred. The amount of base may range from 0 to 0.5 equivalents relative to (RS)-2. The amount of resolving agent may range from 0.5 to 1.2 equivalents relative to (RS)-2.

Regeneration of the resolved (S)— or (R)-2 from the crystallized salt may be effected by treatment of the salt with acid or by use of an acidic ion-exchange resin. Suitable acids include organic and inorganic acids, of which hydrochloric acid and sulfuric acid are preferred.

Recovery of the undesired (R)— or (S)-2 or their mixture (predominantly one enantiomer) from the crystallization mother liquors can be carried out using essentially the same procedures as the one described for regeneration of the resolved (S)— or (R)-2 from the crystallized salt.

The acid anhydride used in the epimerization reaction includes C2-C14 acid anhydrides, of which acetic anhydride, propionic anhydride, butyric anhydride and benzoic anhydride are preferred. The epimerization reaction is carried out in neat acid anhydride or with a co-solvent. The suitable solvents include alkylcarboxylic acids such as acetic acid, propionic acid and butyric acid, aromatic solvents such as toluene and xylene, N,N-dialkylamides such as N,N-dimethylformamide, N,N-dimethylacetamide and 1-methyl-2-pyrrolidinone, and alkyl sulfoxides and sulfones such as dimethyl sulfoxide and sulfolane. The most preferred solvents are acetic acid and toluene. The amount of acid anhydride is about 1.0 to 5.0 equivalents of the acid, more preferably is about 1.0 to 2.0 equivalents. The reaction temperature is between 30 to 150° C., and the preferred temperature is 70-120° C.

Further, according to another aspect of the invention, a process is provided for the preparation of the (S)— and (R)-enantiomers of alpha-ethyl-2-oxo-1-pyrrolidineacetamide of formula 1 from enantiomerically enriched (S)— or (R)-alpha-ethyl-2-oxo-1-pyrrolidineacetic acid of formula 2. The process comprises the following:

i) formation of mixed anhydride (S)— or (R)-3 by reacting (S) or (R)-2 with an alkyl or aryl sulfonyl halogen compound $RSO_2X$ in the presence of a suitable base; and ii) reacting the mixed anhydride with ammonia.

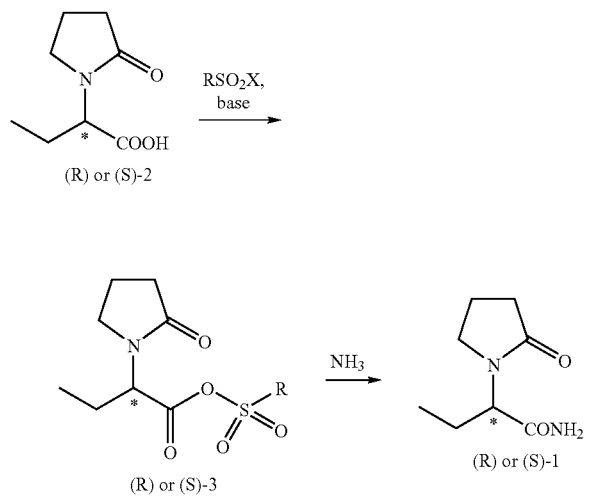

The alkyl or aryl sulfonyl halogen compound used in the mixed anhydride formation step (step i) may be represented as formula $RSO_2X$, in which R represents C1 to C15 alkyl and aryl groups. The preferred R substituents are methyl, ethyl and p-tolyl groups. X represents a halogen atom, for instance F, Cl and Br atoms. The most preferred is Cl. The molar ratio between enantiomerically enriched (S)— or (R)-2 and the activating reagent is about 1:1 to about 1:2, preferably the ratio between about 1:1.1 to about 1:1.3.

In the formation of mixed anhydride (S)— and (R)-3, a suitable base is needed as a hydrogen halide scavenger, which can be selected from organic and inorganic bases, preferably organic bases such as triethylamine, tributylamine, diisopropylethylamine, 4-(dimethylamino)pyridine, pyridine, and more preferably triethylamine and diisopropylethylamine. The molar ratio between enantiomerically enriched (S)— or (R)-2 and the base is about 1:1 to about 1:2, preferably between about 1:1.1 to about 1:1.3.

Although the mixed anhydride (S)— and (R)-3 can be isolated or used directly for the amidation without isolation, it is desirable to use it directly for the reaction with ammonia without isolation.

The solvents used in the reaction can be C1 to C3 chlorinated hydrocarbons, or C2 to C5 nitriles, or C4 to C8 cyclic or acyclic ethers. Preferred solvents include methylene chloride, acetonitrile and tetrahydrofuran.

The temperature for the formation of the mixed anhydride is between −20° C. to 20° C., preferably between −10° C. to 10° C. The mixed anhydride is reacted with ammonia at −10 to 10° C., preferably between −5° C. to 5° C.

Further, according to another aspect of the present invention, a process is provided for the preparation of the (S)— and (R)-enantiomers of alpha-ethyl-2-oxo-1-pyrrolidineacetamide of formula 1 from (RS)-alpha-ethyl-2-oxo-1-pyrrolidineacetic acid of formula 2. The process comprises the following:

i) combining the (RS)-2 with a chiral base (resolving agent) in a resolution solvent and crystallizing from the said mixture the diastereomeric salt of (S)— or (R)-2 and chiral base;

ii) regenerating (S)— or (R)-2 from the crystallized diastereomeric salt by treating with a suitable acid or acidic ion-exchange resin;

iii) optionally regenerating (R)— or (S)-2 or their mixture (predominantly one enantiomer) from the crystallization mother liquor by treating with a suitable acid or acidic ion-exchange resin;

iv) optionally epimerizing (RS)-2 by treating (R)— or (S)-2 or their mixture (predominantly one enantiomer) of step iii with an acid anhydride;

v) optionally converting (RS)-2 of step iv into enantiomerically enriched (S)— or (R)-2 through steps i and ii;

vi) formation of the mixed anhydride (S)— or (R)-3 by reacting (S)— or (R)-2 with an alkyl or aryl sulfonyl halogen compound $RSO_2X$ in the presence of a suitable base; and vii) reacting the mixed anhydride with ammonia.

The process is depicted below:

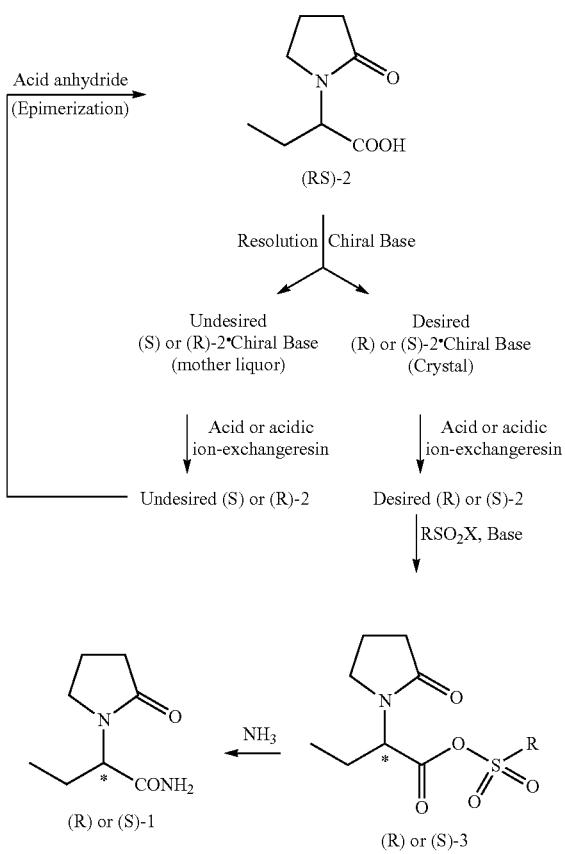

Suitable resolving agents include optically pure bases such as alpha-methylbenzylamine and dehydroabietylamine, of which alpha-methylbenzylamine is preferred. (S)-2 can be prepared by forming the salt with (R)-alpha-methylbenzylamine and the (R)-2 can be prepared by forming the salt with (S)-alpha-methylbenzylamine.

Suitable resolution solvents include water, C1 to C7 alcohols such as methanol, ethanol, isopropanol and butanols, C3 to C7 ketones such as acetone and methyl isobutyl ketone, C2 to C7 nitriles such as acetonitrile, aromatic solvents such as toluene and xylenes, and their mixtures, of which toluene, isopropanol, water and their mixtures are preferred.

The resolution can be carried out in the presence or absence of a non-chiral organic base. Suitable bases include trialkylamine such as trimethylamine, triethylamine and N,N-diisopropylethylamine, pyridine and the like, of which triethylamine and N,N-diisopropylethylamine are preferred. The amount of base may range from 0 to 0.5 equivalents relative to (RS)-2. The amount of resolving agent may range from 0.5 to 1.2 equivalents relative to (RS)-2.

Regeneration of the resolved (S)— or (R)-2 from the crystallized salt may be effected by treatment of the salt with acid or by use of an acidic ion-exchange resin. Suitable acids include organic and inorganic acids, of which hydrochloric acid and sulfuric acid are preferred.

Recovery of the undesired (R)— or (S)-2 or their mixture (predominantly one enantiomer) from the crystallization mother liquors can be carried out using essentially the same procedures as the one described for regeneration of the resolved (R)— or (S)-2 from the crystallized salt.

The acid anhydride used in the epimerization reaction includes C2-C14 acid anhydrides, of which acetic anhydride, propionic anhydride, butyric anhydride and benzoic anhydride are preferred. The epimerization reaction is carried out in neat acid anhydride or with a co-solvent. The suitable solvents include alkylcarboxylic acids such as acetic acid, propionic acid and butyric acid, aromatic solvents such as toluene and xylene, N,N-dialkylamides such as N,N-dimethylformamide, N,N-dimethylacetamide and 1-methyl-2-pyrrolidinone, and alkyl sulfoxides and sulfones such as dimethyl sulfoxide and sulfolane. The most preferred solvents are acetic acid and toluene. The amount of acid anhydride is about 1.0 to 5.0 equivalents of the acid, more preferably is about 1.0 to 2.0 equivalents. The reaction temperature is between 30 to 150° C. and the preferred temperature is 70-120° C.

The alkyl or aryl sulfonyl halogen compound used in the mixed anhydride formation step (step vi) may be represented as formula $RSO_2X$, in which R represents C1 to C15 alkyl and aryl groups. The preferred R substituents are methyl, ethyl and p-tolyl groups. X represents a halogen atom, for instance F, Cl and Br atoms. The most preferred is Cl. The molar ratio between enantiomerically enriched (S)— or (R)-2 and the activating reagent is about 1:1 to about 1:2 and preferably the ratio between about 1:1.1 to about 1:1.3.

In the formation of mixed anhydride (S)— or (R)-3, a suitable base is needed as a hydrogen halide scavenger, which can be selected from organic and inorganic bases, preferably organic bases such as triethylamine, tributylamine, diisopropylethylamine, 4-(dimethylamino)pyridine, pyridine, and more preferably triethylamine and diisopropylethylamine. The molar ratio between enantiomerically enriched (S)— or (R)-2 and the base is about 1:1 to about 1:2, preferably between about 1:1.1 to about 1:1.3.

Although the mixed anhydride (S)— or (R)-3 can be isolated or used directly for the amidation without isolation, it is desirable to use it directly for the reaction with ammonia without isolation.

The solvents used in the reaction can be C1 to C3 chlorinated hydrocarbons, or C2 to C5 nitriles, or C4 to C8 cyclic or acyclic ethers. Preferred solvents include methylene chloride, acetonitrile and tetrahydrofuran.

The temperature for the formation of the mixed anhydride is between −20° C. to 20° C., preferably between −10° C. to 10° C. The mixed anhydride is reacted with ammonia at −10 to 10° C., preferably between −5° C. to 5° C.

The following non-limiting examples further illustrate the manner of carrying out the inventive processes described herein.

EXAMPLE 1

Preparation of (S)-alpha-ethyl-2-oxo-1-pyrrolidineacetamide from (S)-alpha-ethyl-2-oxo-1-pyrrolidineacetic acid A suspension of (s)-alpha-ethyl-2-oxo-1-pyrrolidineacetic acid (45 g, 0.26 mol) in methylene chloride (225 ml) was cooled to 0° C. and triethylamine (53 g, 0.53 mol) and methanesulfonyl chloride (39 g, 0.34 mol) were added dropwise. The mixture was stirred at 0° C. for 30 min., then a stream of ammonia was purged in the solution for 2 hours. The insoluble solids were filtered and the filtrate was concentrated. The product was crystallized from methyl isobutyl ketone to give 36 g (80%) of (S)-alpha-ethyl-2-oxo-1-pyrrolidineacetamide.

EXAMPLE 2

Preparation of (R)-alpha-ethyl-2-oxo-1-pyrrolidineacetamide from (R)-alpha-ethyl-2-oxo-1-pyrrolidineacetic acid A suspension of (R)-alpha-ethyl-2-oxo-1-pyrrolidineacetic acid (35 g, 0.20 mol) in methylene chloride (225 ml) was cooled to 0° C. and triethylamine (41 g, 0.40 mol) and methanesulfonyl chloride (29 g, 0.26 mol) were added dropwise. The mixture was stirred at 0° C. for 30 min., then a stream of ammonia was purged in the solution at 0° C. for 2 hours. The insoluble solids were filtered and the filtrate was concentrated. The product was recrystallized from methyl isobutyl ketone to give 27.5 g (78%) of (R)-alpha-ethyl-2-oxo-1-pyrrolidineacetamide.

EXAMPLE 3

Preparation of (S)-alpha-Ethyl-2-oxo-1-pyrrolidineacetic acid (R)-alpha-methylbenzylamine salt A solution of (R)-alpha-methylbenzylamine (106 g) and triethylamine (89 g) in toluene (100 ml) was added to a suspension of (RS)-alpha-ethyl-2-oxo-1-pyrrolidineacetic acid (300 g, 1.75 mol) in toluene (1 L). The mixture was heated until complete dissolution, cooled to room temperature and stirred for 3 hours. The solids were filtered and rinsed with toluene (300 ml) to give 250 g of (s)-alpha-ethyl-2-oxo-1-pyrrolidineacetic acid (R)-alpha-methylbenzylamine salt. The solids were crystallized from toluene and 205 g (yield 41%) of (S)-alpha-ethyl-2-oxo-1-pyrrolidineacetic acid (R)-alpha-methylbenzylamine salt was obtained. The isolated solid was treated with hydrochloric acid solution and the enantiomerically pure (S)-alpha-ethyl-2-oxo-1-pyrrolidineacetic acid could be isolated in 90% yield.

EXAMPLE 4

Recovery and Epimerization of (R)-alpha-ethyl-2-oxo-1-pyrrolidineacetic acid from the Mother Liquor The combined mother liquors from above were concentrated to half volume and water (200 ml) and 50% sodium hydroxide (52 g) were added sequentially and the mixture was stirred at 20° C. for 30 min. and then was separated. The aqueous layer was washed with toluene (150 ml), acidified with 32% hydrochloric acid until pH=2-3. The resulting suspension was cooled to 0-5° C. and stirred for 2 h. The solids were collected by filtration, and were rinsed with cold water. The damp solids were dried under vacuum oven at 40-50° C. for 4 h to give 160 g of (R)-enriched ethyl-2-oxo-1-pyrrolidineacetic acid. To the above solids, toluene (640 ml) and acetic anhydride (145 g) were added and the mixture was heated to reflux for 10 h. The solution was cooled to 20° C. and stirred for another 2 h. The solids were collected by filtration and rinsed with toluene (150 ml) to give (RS)-alpha-ethyl-2-oxo-1-pyrrolidineacetic acid (152 g).

While the foregoing embodiments provide detailed description of preferred embodiments of the invention, it is to be understood that these are illustrative only of the principles of the invention and not limiting. Furthermore, as many changes can be made to the invention without departing from the scope of the invention, it is intended that all material contained herein be interpreted as illustrative of the invention and not in a limiting sense.

The invention claimed is:

1. A process for preparation of (S)-alpha-ethyl-2-oxo-1-pyrrolidineacetamide or (R)-alpha-ethyl-2-oxo-1-pyrrolidineacetamide from (RS)-alpha-ethyl-2-oxo-1-pyrrolidinacetic acid comprising:
   i) combining the (RS)-alpha-ethyl-2-oxo-1-pyrrolidinacetic acid with a chiral base selected from the group consisting of optically pure: (R)-alpha methylbenzylamine, (S)-alpha methylbenzylamine, (R)-dehydroabietylamine and (S)-dehydroabietylamine in a resolution solvent thereby forming a resolution mixture
   ii) crystallising from the resolution mixture a diastereomeric salt of the chiral base and (S)-alpha-ethyl-2-oxo-1-pyrrolidinacetic acid or the chiral base and (R)-alpha-ethyl-2-oxo-1-pyrrolidinacetic acid;
   iii) treating the diastereomeric salt with a first suitable acid or acidic ion-exchange resin thereby regenerating (S)-alpha-ethyl-2-oxo-1-pyrrolidinacetic acid or (R)-alpha-ethyl-2-oxo-1-pyrrolidinacetic acid;
   iv) reacting, in the presence of a suitable base, a compound of formula $RSO_2X$ with (R)-alpha-ethyl-2-oxo-1-pyrrolidinacetic acid or (S)-alpha-ethyl-2-oxo-1-pyrrolidinacetic acid thereby forming a mixed anhydride; and
   vii) reacting the mixed anhydride with ammonia;
   wherein R is a C1 to C15 alkyl or aryl and X is a halogen.

2. The process according to claim 1 further comprising:
   iii-a) treating a mother liquor obtained from the resolution mixture after crystallising the diastereomeric salt with a second suitable acid or acidic ion-exchange resin thereby regenerating (R)-alpha-ethyl-2-oxo-1-pyrrolidinacetic acid or (S)-alpha-ethyl-2-oxo-1-pyrrolidinacetic acid or a mixture thereof predominantly comprised of either (R)-alpha-ethyl-2-oxo-1-pyrrolidinacetic acid or (S)-alpha-ethyl-2-oxo-1-pyrrolidinacetic acid thereby forming a regeneration mixture;
   iii-b) treating the regeneration mixture with an acid anhydride thereby forming (RS)-alpha-ethyl-2-oxo-1-pyrrolidinacetic acid; and
   iii-c) recycling the (RS)-alpha-ethyl-2-oxo-1-pyrrolidinacetic acid by using the (RS)-alpha-ethyl-2-oxo-1-pyrrolidinacetic acid as a starting material in a process for preparation of (S)-alpha-ethyl-2-oxo-1-pyrrolidineacetamide or (R)-alpha-ethyl-2-oxo-1-pyrrolidineacetamide.

3. The process according to claim 1 wherein the chiral base is (R)-alpha-methylbenzylamine.

4. The process according to claim 1 wherein the chiral base is (S)-alpha methylbenzylamine.

5. The process according to claim 1 wherein the resolution solvent is selected from the group consisting of: water, C1 to C7 alcohols, C3 to C7 ketones, C3 to C7 nitriles, aromatic solvents, and mixtures thereof.

6. The process according to claim 1 wherein the resolution solvent is selected from the group consisting of: water, methanol, ethanol, isopropanol, butanol, acetone, methyl isobutyl ketone, acetonitrile, toluene, xylene, and mixtures thereof.

7. The process according to claim 1 wherein the resolution solvent is toluene, a mixture of toluene and isopropanol or a mixture of toluene and water.

8. The process according to claim 2 wherein the acid anhydride is selected from C2-C14 acid anhydrides.

9. The process according to claim 2 wherein the acid anhydride is acetic anhydride, propionic anhydride or butyric anhydride.

10. The process according to claim 1 wherein R is methyl; ethyl; p-toluene; 2,4,6-trimethylbenzyl; or 2,4,6-trichlorobenzyl, and X is F, Cl or Br.

11. The process according to claim 1 wherein the compound of formula $RSO_2X$ is methanesulfonyl chloride.

12. The process according to claim 1 wherein the compound of formula $RSO_2X$ is p-toluenesulfonyl chloride.

13. The process according to claim 1 wherein the suitable base is selected from the group consisting of: trialkylamines and pyridines.

14. The process according to claim 1 wherein the suitable base is N,N-diisopropylethylamine or triethylamine.

* * * * *